(12) United States Patent
Fiddian-Green

(10) Patent No.: US 6,334,064 B1
(45) Date of Patent: Dec. 25, 2001

(54) REMOTE SENSING TONOMETRIC CATHETER APPARATUS AND METHOD

(75) Inventor: Richard Guy Fiddian-Green, One Marlborough, MA (US)

(73) Assignee: Instrumentarium Corp., Helsinki (FI)

(*) Notice: Subject to any disclaimer, the term of this patent is extended or adjusted under 35 U.S.C. 154(b) by 0 days.

(21) Appl. No.: 08/452,183

(22) Filed: May 26, 1995

Related U.S. Application Data

(63) Continuation of application No. 08/322,081, filed on Oct. 12, 1994, now Pat. No. 5,456,251, which is a continuation of application No. 08/270,988, filed on Jul. 5, 1994, now abandoned, which is a continuation of application No. 08/146,427, filed on Oct. 29, 1993, now abandoned, which is a continuation of application No. 08/014,624, filed on Feb. 8, 1993, now abandoned, which is a continuation of application No. 07/892,631, filed on Jun. 2, 1992, now Pat. No. 5,186,172, which is a continuation of application No. 07/733,071, filed on Jul. 17, 1991, now abandoned, which is a continuation of application No. 07/496,185, filed on Mar. 20, 1990, now abandoned, which is a continuation of application No. 07/380,706, filed on Jul. 13, 1989, now abandoned, which is a continuation of application No. 07/237,287, filed on Aug. 26, 1988, now abandoned, which is a continuation-in-part of application No. 07/994,721, filed on Dec. 22, 1992, now abandoned, which is a continuation of application No. 07/719,098, filed on Jun. 20, 1991, now Pat. No. 5,174,290, which is a continuation of application No. 07/496,186, filed on Mar. 20, 1990, now abandoned, which is a continuation of application No. 07/380,704, filed on Jul. 13, 1989, now abandoned, which is a continuation of application No. 07/237,286, filed on Aug. 26, 1988, now abandoned.

(51) Int. Cl.[7] ................................................ A61B 5/00

(52) U.S. Cl. ...................................... 600/311; 600/504

(58) Field of Search ................................ 128/632, 635, 128/691, 672, 673, 736, 748, 749, 774, 778, 750, 752, 309, 310, 311, 316, 322, 323, 324, 325, 345, 348, 353, 361, 366

(56) References Cited

U.S. PATENT DOCUMENTS

| | | |
|---|---|---|
| 3,043,309 | 7/1962 | McCarthy . |
| 3,339,552 | 9/1967 | Aillon . |
| 3,395,710 | 8/1968 | Stratton et al. . |
| 3,437,088 | 4/1969 | Bielinski . |

(List continued on next page.)

FOREIGN PATENT DOCUMENTS

| | | |
|---|---|---|
| 2 251 685 A | 7/1992 | (GB) . |
| 89 03659 | 8/1989 | (WO) . |

OTHER PUBLICATIONS

Ali, J. et al., "The Cardiorespiratory Effects of Increased Intra-Abdominal Pressure in Diaphragmatic Rupture," *J. Trauma* 33:233–239 (1992).

Anzivino, M.J. et al., "Elevated Systemic to Intramucosal Stomach Wall pH–GAP in Patients with Sepsis," *Chest* 98(2) (1990) Suppl.

Badgwell, J. M. et al., "End–Tidal Carbon Dioxide Pressure in Neonates and Infants Measured by Aspiration and Flow–Through Capnography," *J. Clin. Monit.* 7:285–288 (1991).

(List continued on next page.)

*Primary Examiner*—John P. Lacyk
(74) *Attorney, Agent, or Firm*—Andrus, Sceales, Starke & Sawall, LLP

(57) ABSTRACT

A tonometric device for use in hollow viscus tonometry and remote sensing of patient fluid parameters is disclosed in combination with a secondary apparatus, such as a urinary catheter, a nasogastric sump apparatus, or a feeding tube, for example. The device is capable of monitoring certain critical fluid properties of interest, such as oxygen gases and carbon dioxide gases in the wall tissue itself of the patient's organ, rather than monitoring such properties in a lumen of the organ. A walled sampling chamber, which is preferably an inflated balloon member, is provided on an elongated tube, with provisions for positioning the sampling chamber in direct contact with a wall portion of the patient's internal organ.

20 Claims, 9 Drawing Sheets

U.S. PATENT DOCUMENTS

| | | |
|---|---|---|
| 3,480,003 | 11/1969 | Crites . |
| 3,658,053 | 4/1972 | Fergusson et al. . |
| 3,734,094 | 5/1973 | Calinog . |
| 3,794,041 | 2/1974 | Frei et al. . |
| 3,824,157 | 7/1974 | Macur . |
| 3,983,879 | 10/1976 | Todd . |
| 4,003,705 | 1/1977 | Buzza et al. . |
| 4,016,864 | 4/1977 | Sielaff et al. . |
| 4,020,830 | 5/1977 | Johnson et al. . |
| 4,063,561 | 12/1977 | McKenna . |
| 4,120,292 | 10/1978 | LeBlanc, Jr. et al. . |
| 4,173,981 | 11/1979 | Mortensen . |
| 4,176,659 | 12/1979 | Rolfe . |
| 4,187,856 | 2/1980 | Hall et al. . |
| 4,214,593 | 7/1980 | Imbruce et al. . |
| 4,221,567 * | 9/1980 | Clark et al. .......................... 128/635 |
| 4,233,513 | 11/1980 | Elder et al. . |
| 4,244,377 | 1/1981 | Grams . |
| 4,259,960 | 4/1981 | Taylor . |
| 4,265,249 | 5/1981 | Schindler et al. . |
| 4,273,636 * | 6/1981 | Shimadt et al. ..................... 128/635 |
| 4,304,239 | 12/1981 | Perlia . |
| 4,338,174 * | 7/1982 | Tamura ............................... 128/635 |
| 4,381,011 | 4/1983 | Somers, III . |
| 4,384,586 | 5/1983 | Christiansen . |
| 4,423,739 | 1/1984 | Passaro et al. . |
| 4,432,366 | 2/1984 | Margules . |
| 4,480,190 | 10/1984 | Burough et al. . |
| 4,497,324 | 2/1985 | Sullivan et al. . |
| 4,516,580 | 5/1985 | Polanyi . |
| 4,534,825 | 8/1985 | Koning et al. . |
| 4,576,590 | 3/1986 | Fiddian-Green . |
| 4,580,560 | 4/1986 | Straith . |
| 4,583,969 | 4/1986 | Mortensen . |
| 4,596,931 | 6/1986 | Ehnholm et al. . |
| 4,610,656 | 9/1986 | Mortensen . |
| 4,615,340 | 10/1986 | Cronenberg et al. . |
| 4,643,192 * | 2/1987 | Fiddian-Green ..................... 128/632 |
| 4,671,287 | 6/1987 | Fiddian-Green . |
| 4,716,887 | 1/1988 | Koning et al. . |
| 4,727,730 | 3/1988 | Boiarski et al. . |
| 4,738,668 | 4/1988 | Bellotti et al. . |
| 4,774,956 | 10/1988 | Kruse et al. . |
| 4,784,660 | 11/1988 | Fischell . |
| 4,790,328 | 12/1988 | Young . |
| 4,792,330 | 12/1988 | Lazarus et al. . |
| 4,800,886 | 1/1989 | Nestor . |
| 4,809,710 | 3/1989 | Williamson . |
| 4,830,013 | 5/1989 | Maxwell . |
| 4,850,958 | 7/1989 | Berry et al. . |
| 4,859,858 | 8/1989 | Knodle et al. . |
| 4,859,859 | 8/1989 | Knodle et al. . |
| 4,873,990 | 10/1989 | Holmes et al. . |
| 4,907,166 | 3/1990 | Coreman et al. . |
| 4,914,720 | 4/1990 | Knodle et al. . |
| 4,925,268 | 5/1990 | Iyer et al. . |
| 4,934,369 | 6/1990 | Maxwell . |
| 4,951,669 | 8/1990 | Maxwell et al. . |
| 4,966,141 | 10/1990 | Bacaner et al. . |
| 4,966,578 | 10/1990 | Baier et al. . |
| 4,974,929 | 12/1990 | Curry . |
| 4,981,470 | 1/1991 | Bombeck, IV . |
| 4,998,527 | 3/1991 | Meyer . |
| 5,000,901 | 3/1991 | Iyer et al. . |
| 5,002,055 | 3/1991 | Merki et al. . |
| 5,042,522 | 8/1991 | Coreman et al. . |
| 5,047,208 | 9/1991 | Schweitzer et al. . |
| 5,048,525 | 9/1991 | Maxwell . |
| 5,054,882 | 10/1991 | Riccitelli et al. . |
| 5,057,278 | 10/1991 | Maxwell et al. . |
| 5,067,492 | 11/1991 | Yelderman et al. . |
| 5,095,913 | 3/1992 | Yelderman et al. . |
| 5,119,463 | 6/1992 | Vurek et al. . |
| 5,127,077 | 6/1992 | Iyer et al. . |
| 5,158,083 | 10/1992 | Sacristan et al. . |
| 5,166,990 | 11/1992 | Riccitelli et al. . |
| 5,167,237 | 12/1992 | Rabin et al. . |
| 5,171,029 | 12/1992 | Maxwell et al. . |
| 5,174,290 * | 12/1992 | Fiddian-Green ..................... 128/632 |
| 5,184,618 | 2/1993 | Wider et al. . |
| 5,186,172 | 2/1993 | Fiddian-Green . |
| 5,225,063 | 7/1993 | Gumbrecht et al. . |
| 5,251,633 | 10/1993 | Wunderling et al. . |
| 5,319,978 | 6/1994 | Grudzien, Jr. . |
| 5,328,848 | 7/1994 | Fong et al. . |
| 5,345,932 | 9/1994 | Yafuso et al. . |
| 5,355,880 | 10/1994 | Thomas et al. . |
| 5,434,084 | 7/1995 | Burgess, Jr. . |
| 5,630,413 | 5/1997 | Thomas et al. . |

OTHER PUBLICATIONS

Bagley, N.A. et al., "Urodynamic Evaluation of Voluntary Detrusor Response in Healthy Subjects," *Arch. Phys. Med. Rehabil.* 66:160–163 (1985).

Barbalias, G.A. et al., "Rectal Pressure Measurements and Intra–Abdominal Pressure Changes".

Barnes, G.E. et al., "Cardiovascular Responses to Elevation of Intra–Abdominal Hydrostatic Pressure," *Am. J. Physiol.* 48:R208–R213 (1985).

Bass, B.L., et al., "Intraluminal $pCO_2$: A reliable Indicator of Intestinal Ischemia," *J. Surg. Res.* 39:351–360 (1985).

Bergofsky, E.A., "Determination of Tissue $O_2$ Tensions by Hollow Visceral Tonometers: Effect of Breathing in Enriched $O_2$ Mixtures" *J. Clin. Invest.* 43:193–200 (1964).

Boda, D. et al., "Gastrotonometry an Aid to the Control of Ventilation During Artificial Respiration," *Lancet* Jan. 24, 1959 pp. 181 and 182.

Bradley, S.E. et al., "The Effect of Increased Intra–Abdominal Pressure on Renal Function in Man," *J. Clin. Invest.* 26:1010–1022 (1947).

Brantigan, J.W. et al., "A Telfon Membrane for Measurement of Blood and Intramyocardial Gas Tensions by Mass Spectroscopy," *J. Applied Physiol.* 32:276–282 (1972).

Bryant, T.N. et al., "Indirect Monitoring and Analysis of Truncal Stress Over Extended Time Periods," *J. Biomed. Eng.* 8:172–174 (1986).

Buchler, B. et al., "Effects of Pleural Pressure and Abdominal Pressure on Diaphragmatic Blood Flow," *J. Applied Physiol.* 58:691–697 (1985).

Burchard, K.W. et al., "Positive and Expiratory Pressure with Increased Intra–Abdominal Pressure," *SGO* 161:313–318 (1984).

Cadwell, C.B. et al., "Evaluation of Intra–Abdominal Pressure and Renal Hemodynamics," *Current Surg.* 43:495–498 (1986).

Cadwell, C.B. et al., "Changes in Visceral Blood Flow with Elevated Intraabdominal Pressure," *J. Surg. Res.* 43:14–20 (1987).

Calloway, D.H., "Gas in the Alimentary Canal," Chapter 137 in *Handbook of Physiology—Alimentary Canal*, V:2839–2859.

Celoria, G. et al., "Oliguria from High Intra–Abdominal Pressure Secondary to Ovarian Mass," *Crit. Care Med.* 15:78–79 (1987).

Cerabona, T. et al., "Urinary Bladder Measurements of Intra–Abdominal Pressure (IAP) in Ascitic Cirrhotics Predictive of Hemodynamic and Renal Function," *Crit. Care Med.* 16:431 (1988).

Collee, G.G. et al., "Beside Measurement of Intra–Abdominal Pressure (IAP) Via an Indwelling Naso–Gastric Tube: Clinical Validation of the Technique," *Intensive Care Med.* 19:478–480 (1993).

Cresswell, A.G. et al., "Observations on Intra–Abdominal Pressure and Patterns of Abdominal Intra–Muscular Activity in Man," *Acta. Physiol. Scand.* 144:409–418 (1992).

Cresswell, A. G., et al., "Intra–Abdominal Pressure and Patterns of Abdominal Muscle Activation in Isometric Trunk Flexion and Extension," *Abstracts—International Society of Biomechanics XII Congress* p. 998 (1989).

Cullen, D.J. et al., "Cardiovascular, Pulmonary, and Renal Effects of Massively Increased Intra–Abdominal Pressure in Critically Ill Patients," *Crit. Care Med.* 17:118–121 (1989).

Daly, R.C. et al., Abdominal Reexploration for Increased Intra–Abdominal Pressure and Acute.

Oliguric Renal Failures, *Contemp. Surg.* 35:11–18 (1989).

Dawson, A.M., "Small Bowel Tonometry: Assessment of Small Mucosal Oxygen Tension in Dog and Man," *Nature* 206:943–944 (1965).

Diebel, L.N. et al., "Effect of Increased Intra–Abdominal Pressure on Mesenteric Arterial and Intestinal Mucosal Blood Flow," *J. Trauma* 33(1):45–49 (1992).

Diebel, L. et al., "Effect of Intra–Abdominal Pressure on Abdominal Wall Blood Flow," *Am. Surg.* 58:573–576 (1992).

Diebel, L.N. et al., "Effect on Increased Intra–Abdominal Pressure on Hepatic Arterial, Portal Venous, and Hepatic Microcirculatory Blood Flow," *J. Trauma* 33:279–283 (1992).

Ducas, J. et al., "Thoracicoabdominal Mechanics During Resuscitation Maneuvers," *Chest* 84/4 (1983).

Elder, J.B. et al., "Intragastric $PCO_2$ in Man and Calculated Gastric Bicarbonate Concentrations: Effect of Carbenoxolone Sodium," *Carbenoxolone Effect on Intragastric $PCO_2$ and $HCO_3$* pp. 19–25 (1980).

Emerson, H., "Intra–Abdominal Pressures," *Arch. Int. Med.* 7:754–784 (1911).

Fairbank, J.C. et al., "Intraabdominal Pressure Rise During Weight Lifting as an Objective Measure of Low–Back Pain," *Spine* 5(2):179–184 (1980).

Fantl, J. et al., "Efficacy of Bladder Training in Older Women with Urinary Incontinence," *JAMA* 265(5):609–613 (1991).

Fiddian–Green presentation "Advances in ICU Monitoring Techniques," Oct. 25–29, 1992.

Fiddian–Green, R.G., "pH–Gap: A Measurement for Estimating the Presence or Absence of Intestinal Mucosal Ischemia Independently of Disturbances in Systemic Acid Base Balance," (Abstract) ESSR Meeting in Finland (May 23–26, 1983).

Fiddian–Green, R.G., "Should Measurement of Tissue pH and $PO_2$ be Included in the Routine Monitoring of Intensive Care Unit Patients?" *Crit. Care Med.* 19:141–143 (1991).

Fietsam, R. et al., Intra–Abdominal Compartment Syndrome as a Complication of Ruptured Abdominal Aortic Aneurysm Repair, *Am. Surg.* 55:396–402 (1989).

Fischer, M., Raised Intra–Abdominal Pressure, Renal Failure and the Bumble Bee, *Int. Care Med.* 16:285–286 (1990).

Guazzi, M. et al., "Negative Influences of Ascites on the Cardiac Function of Cirrhotic Patients," *Am. J. Med.* 59:165–170 (1975).

Gutierez, G. et al. "Gastric Intramucosal pH as a Therapeutic Index of Tissue Oxygenation in Critically Ill Patients" *The Lancet* 339:195–199 (1992).

Guyton, A.C. et al., "Quantitative Aspects of the Collapse Factor in Relation to Venous Return," *Am. J. Physiol.* 177:523–527 (1954).

Hamilton, J.D. et al., "Observations upon Small Gut "Mucosal" $pO_2$ $pCO_2$ in Anesthetized Dogs," *Gastroenterology* 55:52–60 (1968).

Hargreaves, D.M., "Raised Intra–Abdominal Pressure and Renal Failure," *Anaesthesia* 46:796 (1991).

Harman, K.P. et al., "Elevated Intra–Abdominal Pressure and Renal Function," *Ann. Sur.* 196:594–597 (1982).

Higgins, J.R. et al., "Tension Pneumoperitoneum: A Surgical Emergency," *Br. J. Hos. Med.* pp. 160–161 (1988).

Hoffman, R.A. et al., "End–Tidal Carbon Dioxide in Critically Ill Patients during Changes in Mechanical Ventilation," *Am. Ref. Respir. Dis.* 140:1265–1268 (1989).

Hunt, T.K. "A New Method of Determining Tissue Oxygen Tension," *Lancet* 1370–1371 (1964).

Iberti, T.J. et al., "Determination of Intra–Abdominal Pressure Using a Transurethral Bladder Catheter: Clinical Validation of the Technique," *Anesthesiology* 70:47–50 (1989).

Jacques, T., et al., "Improvement of Renal Function after Relief of Raised Intra–Abdominal Pressure due to Traumatic Retroperitoneal Haematoma," *Anaesth. Intens. Care.* 16:478–494 (1988).

Jellinek, H. et al., "Arterial to End–Tidal $CO_2$ Tension Difference After Bilateral Lung Transplantation," *Crit. Care Med.* 21(7):1035–1040 (1993).

Kaback, K. et al. "Letters *JAMA*" *JAMA* 254:1035 (1985).

Kashtan, J. et al., "Haemodynamic Effects of Increased Abdominal Pressure," *J. Surg. Res.* 30:249–255 (1981).

Kelly, K. et al., "A Simple Non–Invasive Technique to Measure Intra–Abdominal Pressure," *Crit. Care* p. 366 (1987).

Kelly, K.M. et al., "A Simple Non–Invasive Technique to Measure Intra–Abdominal Pressure," (Abstracts) p. 371.

Kivilaakso, E., et al. "Gastric Blood Flow, Tissure Gas Tension and Microvascular Changes During Hemorrhage –Induced Stress Ulceration in the Pig," *Am. J. Surg.* 143:322–330 (1982).

Kivisaari, J. et al., "Use of Silastic Tube and Capillary Sampling Technic in the Measurement of Tissue $PO_2$ and $PCO_2$," *Am. J. Surg.* 125:623–627 (1973).

Kram, H.B. et al., "Noninvasive Measurement of Tissue Carbon Dioxide Tension Using a Fiberoptic Conjunctival Sensor: Effects of Respiratory and Metabolic Alkalosis and Acidosis," *Crit. Care Med.* 16:280–284 (1988).

Kron, I.L. et al., "The Measurement of Intra–Abdominal Pressure as a Criterion of Abdominal Re–Exploration," *Ann. Surg.* 199:28–30 (1984).

Lacey, S.R., et al., "The Relative Merits of Various Methods of Indirect Measurement of Intraabdominal Pressure as a Guide to Closure of Abdominal Wall Defects," *J. Ped. Surg.* 22(12):1207–1211 (1987).

Landers, B.R. et al., "Response of Porcine Lower Esophageal Sphincter to Increasing Intraabdominal Pressure," *Dig. Dis. Sci.* 32:272–279 (1987).

Lawson, D. et al., "Stability and Long–Term Durability of Raman Spectroscopy," *J. Clin. Monit.* 9:241–151 (1993).

Lenz, G. et al., "Capnometry for Continuous Postoperative Monitoring of Nonintubated, Spontaneously Breathing Patients," *J. Clin. Monit.* 7:245–248 (1991).

Leon, A. et al., "Septic Shock: Does Gastric Mucosal Tonometry Assess Tissue Oxygenation?" 79(3A) (1993).

Le Roith, D. et al., "The Effect of Abdominal Pressure on Plasma Antidiuretic Hormone in the Dog," *J. Sur. Res.* 32:65–69 (1982).

Luiz, T. et al., "Veranderungen der Ventilation Wahrend Laparoskopischer Cholezystektomie," *Anaesthesist* 41:520–529 (1992).

Lumsden, T. et al., "The PB3300 Intraarterial Blood Gas Monitoring System," *J. Clin. Monit.* 10(1):59–66 (1994).

Martinez–Pellus, A.E. et al., "Can Selective Digestive Decontamination Avoid the Endotoxemia and Cytokine Activation Promoted by Cardiopulmonary Bypass?" *Crit. Care Med.* 21:1684–1691 (1993).

McCarthy, T.A., "Validity of Rectal Pressure Measurements as Indication of Intra–Abdominal Pressure Changes During Urodynamic Evaluation," *Urology* 6:657–660 (1982).

McGee, Lemuel et al., "The Carbon Dioxide Tension and Acid–Base Balance of Jejunal Secretions in Man," 893–904 (1941).

McIver, M.A. et al., "Gaseous Exchange Between the Blood and the Lumen of the Stomach and Intestines," *Am. J. Physiol.* 76(1):92–111 (1926).

Motew, M. et al., "Cardiovascular Effects and Acid–Base and Blood Gas Changes during Laparoscopy," *Am. J. Obstet, Gynecol.* 115:1002–1012 (1972).

Nielsen, J.R. et al., "The Absorption Laws for Gases in the Infra–Red" *Rev. Modern Physics.* 16(3&4):307–324 (1944).

Niemczyk, T.M. et al., "Multichannel Raman Spectroscopy Tackles Industrial Problems," *Laser Focus World* Mar.: 85, 86, 88, 90, 92, 95, 97 and 98 (1993).

Noc, M. et al., "Comparison of Gastric Luminal and Gastric Wall $PCO_2$ During Hemorrhagic Shock," *Cir. Shock* 40:194–199 (1993).

Nordin, M. et al., "Intra–Abdominal Pressure Measurements Using a Wireless Radio Pressure Pill and Two Wire Connected Pressure Transducers: A Comparison," *Scand. J. Rehab. Med.* 16:139–146 (1984).

O'Leary M.J. et al., "Acute Renal Failure in Association with Pneumatic Antishock Garment and with Tense Ascites," *Anesthesia* 46:326–327 (1991).

Overholt, R.H., "Intraperitoneal Pressure," *Arch. Surg.* 22(5):691–703 (1931).

Paulus, D.A., "Capnography," *Int'l. Anes. Clin.* 27(3):167–174 (1989).

Platell, C.F. et al., "Impaired Renal Function Due to Raised Intraabdominal Pressure," *Intensive Care Med.* 16:328–329 (1990).

Raemer, D.B. et al., "Variation in $PCO_2$ between Arterial Blood and Peak Expired Gas during Anesthesia," *Anest. Analg.* 62:1065–1069 (1983).

Raemer, D.B. et al., "Monitoring Anesthetic and Respiratory Gases," Chapter 14 *Monitoring in Anesthesia and Critical Care Medicine* pp. 373–386.

Raemer, D.B. et al., "Accuracy of End–Tidal Carbon Dioxide Tension Analyzers," *J. Clin. Monit.* 7(2):195–208 (1991).

Richards, W.O. et al., "Acute Renal Failure Associated with Increased Intra–Abdominal Pressure," *Ann. Surg.* 197:183–187 (1983).

Ring, J.C. et al., "Effects of Acute Tense Abdominal Distension on Regional Blood Flow and Renal Function," *Critical Care Med.* 12:222 (1984).

Rippe M.D., J.M., *Medicine* 2nd ed. pp. 210–214.

Rodrigues, A.A. et al., "Therapeutic Exercise in Chronic Neck and Back Pain," *Arch. Phys. Med. Rehab.* 73:870–875 (1992).

Rowen, D. et al., "An Investigation of Bladder–Urethral Function by Pressure–Flow Studies," *BioMed Eng.* 304–308 (1972).

Roy, J. et al., "An Improved Nasal Prong Apparatus for End–Tidal Carbon Dioxide Monitoring in Awake, Sedated Patients," *J. Clin. Monit.* 7(3):249–252 (1991).

Rune, S.J. et al., "Carbon Dioxide Tensions in the Proximal Part of the Canine Gastrointestinal Tract," *Gastroenterology* 56:758–762 (1969).

Rune, S.J., "Acid–Base Parameters of Duodenal Contents in Man," *Gastroenterology* 62:533–539 (1972).

Salzman, A.L. et al., "Air Tonometry: A New Method for Determination of Gastrointestinal Mucosal $PCO_2$," *Crit. Care Med.* 21(4):S202 (1993).

Savino, J.A. et al., "Manipulation of Ascitic Fluid Pressure in Cirrhotics to Optimize Hemodynamic and Renal Function," *Ann. Surg.* 208:504–511 (1988).

Scannell, G. et al., "Tissue Oximetry in Hemorrhagic Shock and Resuscitation: Gastric But not Rectal Submucosal $pO_2$ Correlates with Gut Translocation," *Crit. Care Med.* 22:A187 (1993) (abstract).

Schwarz, C. et al., "Sodium–Taurocholate–Induced Acute Necrotizing Pancreatitis does not Affect Jejunal Oxygenation in Pigs," *Crit. Care Med.* 22:135–141 (1994).

Severinghaus, J.W. et al., "Correction Factors for Infrared Carbon Dioxide Pressure Broadening by Nitrogen, Nitrous Oxide and Cyclopropane," *Anesthesiology* 22(3):429–432 (1961).

Shafik, A. et al., "Dynamic Study of Rectal Detrusor Activity at Defecation," *Digestion* 49:167–174 (1991).

Shafik, A., "Straining Urethral Reflex: Description of a Reflex and its Clinical Significance," *Acta. Nat.* 140:104–107 (1991).

Shafik, A., "Esophago–Rectal Reflex: Description and Clinical Significance," *Int. Surg.* 78:83–85 (1993).

Shafik, A., "Straining Puborectalis Reflex: Description and Significance of a 'New ' Reflex," *Anatomical Record* 229:281–284 (1991).

Shelly, M.P. et al., "Haemodynamic Effects Following Surgical Release of Increased Intra–Abdominal Pressure," *Br. J. Anaesth.* 59:800–805 (1987).

Shenasky, J.H. et al., "The Renal Haemodynamic and Functional Effects of External Counterpressure," *Surg. Gynecol. Obstet.* 134:253–258 (1972).

Siesjo, B.K., "A Method for Continuous Measurement of the Carbon Dioxide Tension on the Cerebral Cortex," *Acta Physiol. Scand.* 51:297–313 (1961).

Sloan, S. et al., "Determinants of Gastroesophageal Junction Incompetence: Hiatal Hernia, Lower Esophageal Sphincter, or Both?," *Am. College of Phys.* 117:977–982 (1992).

Smith, J.H. et al., "Reversal of Post–Operative Anuria by Decompressive Celiotomy," *Arch. Int. Med.* 145:553–554 (1985).

Smith–Wright, D.L. et al., "The Hemodynamic Effects of Dopamine and/or Volume Expansion in Acute Tense Abdominal Distension," *Crit. Care Med.* 270 (1985).

Starlinger, M. et al., "H+ Back Diffusion Stimulating Gastric Mucosal Blood Flow in the Rabbit Fundus," *Surgery* 89:232–236 (1981).

Stock, M.C., "Noninvasive Carbon Dixoide Monitoring: Capnography," *Crit. Care Clin.* 4(3):511–526 (1988).

Stone, H.H. et al., "Renal Decapsulation in the Prevention of Post–Ischemic Oliguria," *Ann. Surg.* 186:343–355 (1977).

Sussman, A.M. et al., "Effect of Positive End–Expiratory Pressure on Intra–Abdominal Pressure," *South Med. J.* 84:697–700 (1991).

Tang, W. et al., "Gastric Intramural $PCO_2$ is Highly Correlated with Gastric Blood Flow During Both Menorrhagic and Anaphylactic Shock," *Crit. Care Med.* A108 (1994).

Thompson, D.G., et al., "Normal Patterns of Human Upper Small Bowel Motor Activity Recorded by Prolonged Radiotelemetry," *Gut* 21:500–506 (1980).

van Gool, J.D. et al., "Measurement of Intravesical and Rectal Pressures Simultaneously with Electromyography of Anal Sphincter in Children with Myelomeningocele," *Develop. Med. Child Neurol.* 18:287–301 (1976).

Vurek, G.G. et al., "A Fiber Optic $PCO_2$ Sensor," *Annal. Biomed. Eng.* 2:499–510 (1993).

Walton, D.M. "Continuous Monitoring of Blood pH, $PCO_2$ and $PO_2$ in Clinical Practice," Fifth ISA Biomedical Sciences Instrumentations Supposium, Denver, CO, May 1970 pp. 155–158.

Westenskow, D.R. et al., "Clinical Evaluation of Raman Scattering–Multiple Gas Analyzer for the Operating Room," *Anesthesiology* 70:350–355 (1989).

Westenskow, D.R. et al., "Raman Scattering for Respiratory Gas Monitoring in the Operating Room: Advantages, Specifications, and Future Advances," *Biomed. Instru. Tech.* Nov./Dec.:485–489 (1989).

Westenskow, D.R. et al., "Can the Raman Scattering Analyzer Compete with Mass Spectrometers: An Affirmative Reply," *J. Clin. Monit.* 5(1):34–36 (1989).

\* cited by examiner

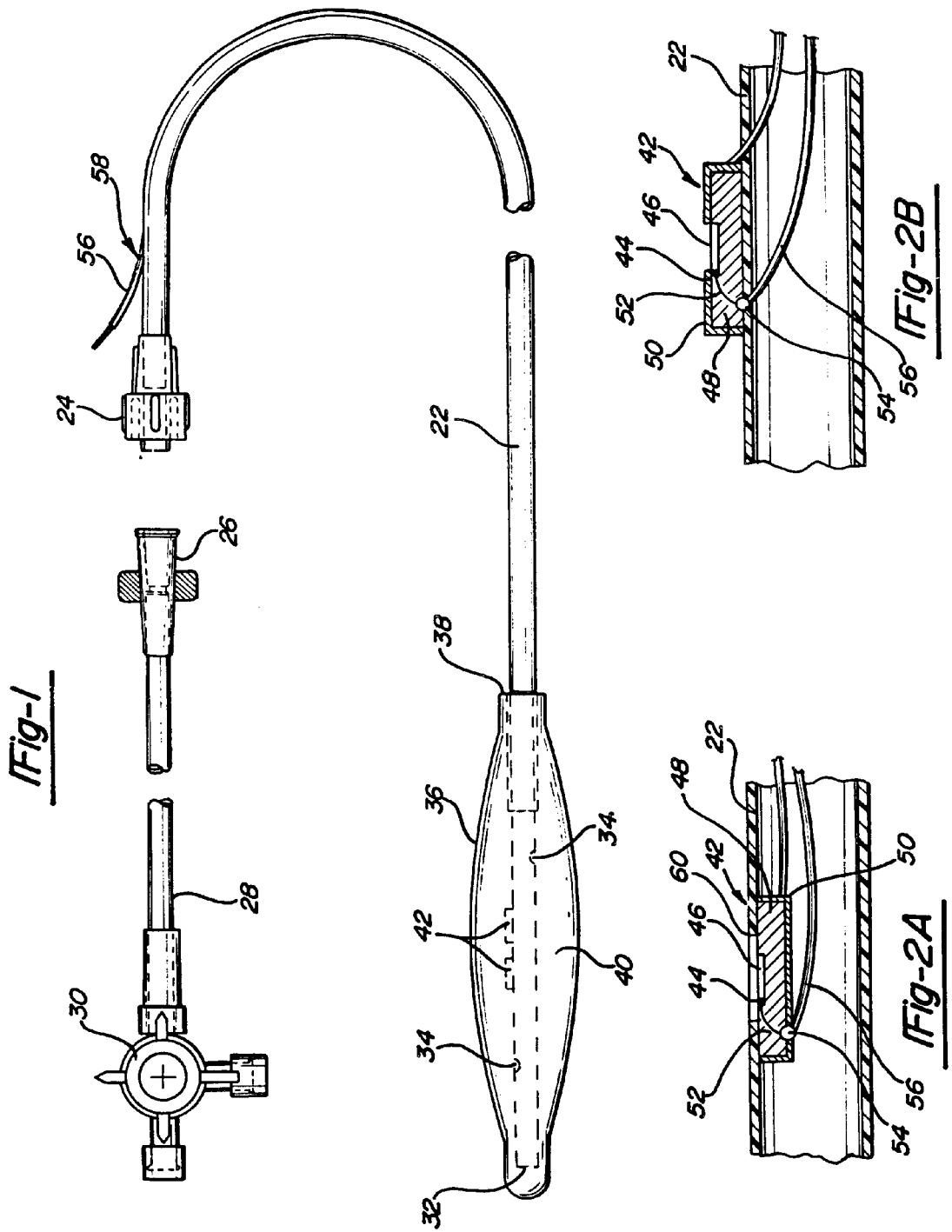

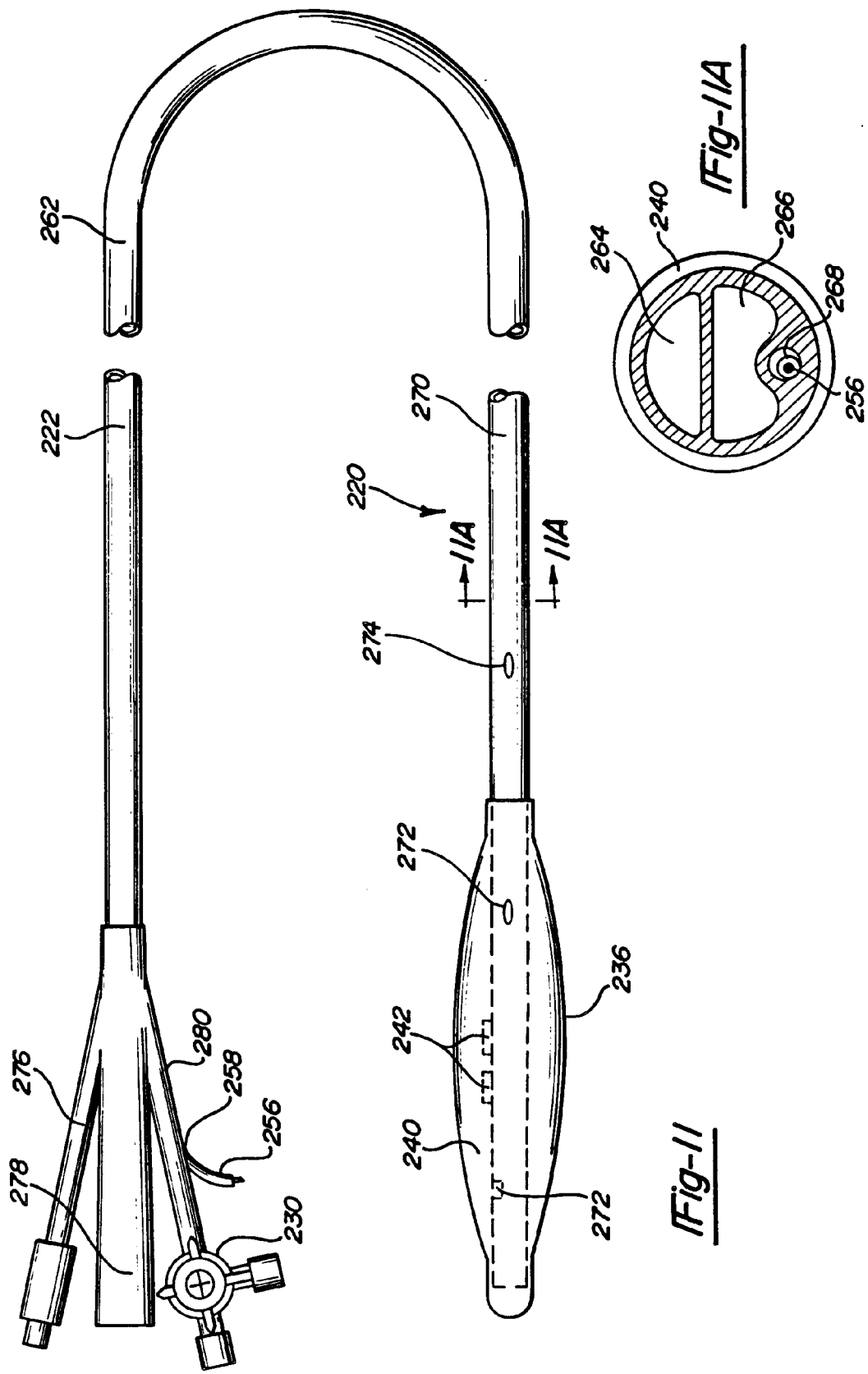

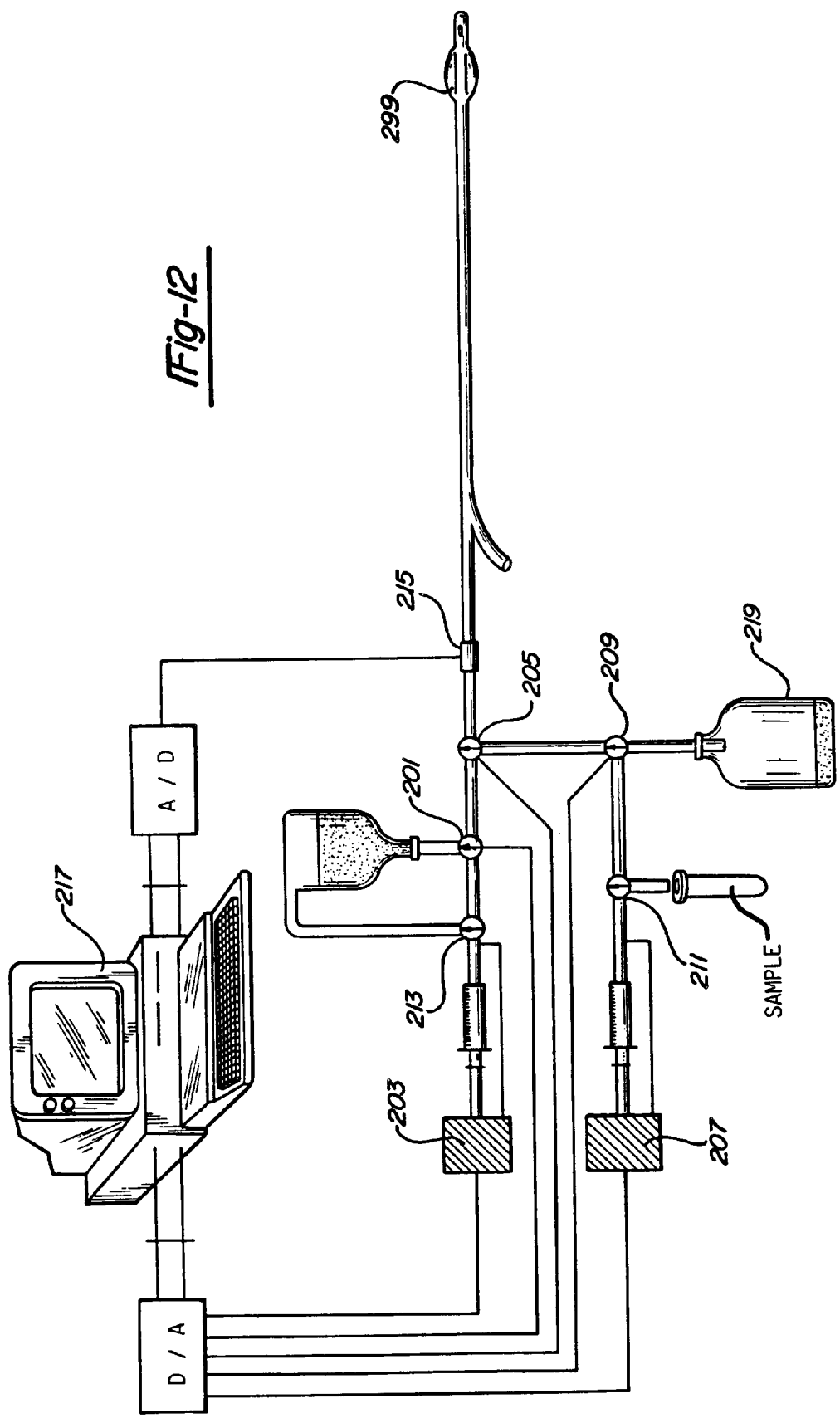

REMOTE SENSING TONOMETRIC CATHETER APPARATUS AND METHOD

This is a continuation of U.S. patent application Ser. No. 08/322,081, filed Oct. 12, 1994 now U.S. Pat. No. 5,456, 251; which is a cont. of Ser. No. 08/270,988 filed Jul. 5, 1994 now abandoned; which is a cont. of Ser. No. 08/146, 427 filed Oct. 29, 1993 now abandoned; which is a cont. of Ser. No. 08/014,624 filed Feb. 8, 1993 now abandoned; which is a cont. of Ser. No. 07/892,631 filed Jun. 2, 1992 (U.S. Pat. No. 5,186,172); which is a cont. of Ser. No. 07/733,071 filed Jul. 17, 1991 now abandoned; which is a cont. of Ser. No. 07/496,185 filed Mar. 20, 1990 now abandoned; which is a cont. of Ser. No. 07/380,706 filed Jul. 13, 1989 now abandoned; which is a cont. of Ser. No. 07/237,287 filed Aug. 26, 1988 now abandoned; which is a CIP of Ser. No. 07/994,721 filed Dec. 22, 1992 now abandoned; which is a cont. of Ser. No. 07/719,098 filed Jun. 20, 1991 (U.S. Pat. No. 5,174,290); which is a cont. of Ser. No. 07/496,186 filed Mar. 20, 1990 now abandoned; which is a cont. of Ser. No. 07/380,704 filed Jul. 13, 1989 now abandoned; which is a cont. of Ser. No. 07/237,286 filed Aug. 26, 1988 now abandoned.

BACKGROUND AND SUMMARY OF THE INVENTION

This invention relates to medical diagnostic equipment and methods and is particularly concerned with hollow viscus tonometry and remote electronic and optical sensing.

The prior art (see U.S. Pat. No. 4,643,192) has recognized that intestinal ischemia, and to a lesser degree, stress ulceration, are two problems that plague physicians involved in the management of patients in intensive care units. Intestinal ischemia, in particular, has an insidious onset and may not be detected until days after the intestine has become completely and irreversibly compromised. A delay in the diagnosis of intestinal ischemia may have devastating consequences for a patient. The availability of means for early diagnosis and management of patients with these problems would have immediate applicability in all intensive care units, especially where the procedure can be conveniently conducted with reasonable safety and reliability.

It has been established that a fall in the intramucosal pH may precede the development of intestinal ischemia and stress ulceration. As I reported in my prior U.S. Pat. No. 4,643,192, expressly incorporated herein by reference, entitled "Hollow Viscus Tonometry" a fall in intramucosal pH also occurs within minutes of inducing intestinal ischemia in dogs. The fall in pH in intestinal mucosa, and hence the likelihood of ischemia or stress ulceration, can be reliably calculated from a $pCO_2$ (partial pressure of $CO_2$), or other indicia of pH, in luminal fluid and the bicarbonate concentration in arterial blood. The method of calculating the pH in intestinal mucosal tissue, pursuant to principles of my prior patent, has been validated by directed measurements under a variety of conditions simulating clinical problems. A correlation coefficient in the order of 0.92 to 0.95 has been obtained in each of 16 dogs. The validity of the procedure is inherently extensible to humans, and indeed may also be useful in assessing the vitality of other hollow organs and tissue. See R. G. Fiddian-Green et al. "Splanchnic Ischemia and Multiple Organ Failure".

To measure the $pCo_2$ in the lumen of the gut it has heretofore been necessary to obtain and remove a sample of fluid that has been in contact with the wall of the gut for a certain time period, usually at least half an hour. It has now been observed that it is somewhat difficult to manually aspirate the sampling fluid or medium from a tonometric catheter located in the gut or other internal focus with any consistency. It is much easier to obtain such samples from the stomach, but samples obtained from the stomach frequently contain foreign material that can damage a gas analyzer.

As taught in my prior patent, the desired sample or samples can be obtained from the gut using a catheter tube (called a tonometric catheter) having a walled sampling chamber on the tube with the sampling chamber being in sample-specific communication with the hollow interior of the tube. The wall of the sampling chamber comprises a material which is substantially impermeable to liquid yet is highly permeable to gas. One suitable material is polydimethylsiloxane elastomer.

In use the catheter is introduced into a patient to place the sampling chamber at a desired site within the gut. An aspirating liquid or medium is employed to fill the interior of the sampling chamber. The sampling chamber is left in place at the desired sampling site long enough to allow the gases present to diffuse through the wall of the sampling chamber into the aspirating liquid. The time should be long enough for the gases to equilibrate. The liquid impermeable nature of the sample chamber wall material prevents both the aspirating liquid from leaking out of the chamber and also the intrusion of any liquids into the aspirating liquid. After the appropriate or desired amount of placement time has elapsed the aspirating liquid is aspirated along with the gases which have diffused into it. The sample thus obtained is analyzed for gas content, in particular for $pCO_2$. In this way the $pCO_2$ within the lumen of the gut can be reliably measured with the fluid being free from lumenal debris.

In carrying out the diagnostic method taught in my prior patent the $pCO_2$ measurement is utilized in conjunction with a measurement of the bicarbonate ion concentration ($HCO_3^-$) in an arterial blood sample of the patient for determining the pH of the tract wall.

Depending upon the particular condition of a given patient, the catheter may be left in place and samples may be taken at periodic intervals so that pH values may be periodically calculated. The procedure has a high reliability in accurately determining the adequacy of organ tissue oxygenation, and diagnosing intestinal ischemia in its incipient stages. Such determination or detection can be useful in treating the patient so that the potentially devastating consequences resulting from less timely detection may often be avoided.

While the sampling techniques taught in my prior patent have provided highly accurate and reliable results, it has now been observed that there are instances (in the care of the critically ill in intensive care units, for example) in which remote sensing of the organ or organ-wall condition and automatic calculation of the organ or organ-wall pH would be advantageous and easier to effectuate. This method would thus partially or totally eliminate the need for the somewhat cumbersome aspiration of the sampling fluid or medium which fills the sampling chamber; it may also eliminate the need for the sampling chamber to be in sampling-medium communication with any other part of the device. There is also a need to extend the benefits of tonometric sampling and sensing to other internal hollow viscous organs. To this end, there is a need for new and different tonometric devices specifically adapted to allow my sensing and sampling techniques to be performed with ease in a clinical environment, and in combination with other procedures.

The importance and significance of determining the pH of the wall of a given hollow viscous organ has been recently dramatically magnified as a result of the recent recognition that the pH of the wall of a given organ can be employed to accurately evaluate the vitality and/or stability of that organ as well as others; this is in contrast to merely determining whether such an organ is experiencing an ischemic event. Further, certain organs can be selected for monitoring, either alone or in combination, and evaluation of this organ or these organs can aid in predicting the overall condition of the patient, or the onset of a multitude of pathologies, including predicting or identifying such events as multiple organ failure. Such a methodology can be employed to greatly enhance and supplement the monitoring of the critically ill, for example.

In one aspect, the present invention provides a new apparatus and method for remotely sensing organ condition and conveying an electromagnetic signal, e.g. an electrical current or optical signal, to an electronic or optical apparatus located outside the organ under investigation. In one embodiment, a chemically sensitive electronic transducer (or plurality of transducers), such as a field effect transistor, is attached to a tonometric catheter for introduction into the organ along with the tonometric catheter. The first electronic sensor, preferably non-temperature, generates and conveys an electromagnetic signal indicative of some desired aspect of organ condition, e.g., indicative of the $pCO_2$, pH and/or $pO_2$ level of the organ or organ-wall. For example, in one preferred embodiment, mean ambient $pCO_2$, pH and/or $pO_2$ of lumenal fluid or the like is measured or monitored via wire or other suitable electromagnetic energy conveying means to an electronic circuit which interprets the electromagnetic signal and produces a report of the organ condition. The electronic circuit may include an input for receiving a separately determined signal indicative of the blood pH of the patient. Using this $pCO_2$, pH and/or $pO_2$ measurement along with blood (preferably arterial) pH data, the electronic circuit determines the pH of the organ wall under test and thereby provides information for determining the organ's current condition or perhaps predicting the organ's future condition. The electronic circuit may be suitably constructed from analog components, digital components or both.

In another embodiment, a pH, $pCO_2$ or $pO_2$ sensitive colorimetric substance is injected into an area adjacent to the organ, e.g., into the sampling chamber of the tonometric catheter, and an optical sensor is employed to detect color change in order to determine the pH of the wall of that organ. The optical sensor can either be disposed in or on the tonometric catheter for introduction into the area adjacent the organ or it may be disposed outside the organ with fiber optic cable optically coupling the sensor to the tonometric catheter site at which the pH sensitive substance has been injected.

In another aspect the present invention provides a variety of new and different tonometric catheter devices for sensing and/or sampling a fluid or gas property (such as pH, $pO_2$, $pCO_2$, and the like) which is indicative of the condition of an internal organ, in conjunction or combination with a walled catheter tube adapted for delivery or draining fluids, such as nasogastric tubes, urinary catheters, ureteric catheters, intestinal feeding tubes, wound or abdominal drains (suction or regular) and biliary tubes, catheters and stents, with or without remote sensing means for pH, $pCO_2$ and/or $pO_2$.

In still another aspect or embodiment, the device employs two separate walled catheter tubes, one tonometric catheter tube for the measurement of a fluid or gas property, that is in communication with the sampling chamber; and a second walled catheter tube adapted for delivering or draining fluids.

In yet another aspect or embodiment, the device employs a walled sampling chamber in communication with a sensing means, and a second walled catheter tube adapted for delivering or draining fluids.

Optionally, when a non-temperature sensing-means is employed, a second sensing-means may be employed as well.

For a more complete understanding of the invention, its objects and advantages, reference may be had to the following specification and to the accompanying drawings. Also, see my co-pending and commonly assigned applications filed of even date herewith entitled "Tonometric Catheter Combination" and "Hollow Viscus and Solid Organ Tonometry", bearing respective Ser. Nos. 237,287 now abandoned and 237,288 now abandoned, both of which are completely and expressly incorporated herein by reference.

BRIEF DESCRIPTION OF THE DRAWINGS

FIG. 1 is a plan view of a first embodiment of the tonometric catheter;

FIG. 2A is a partial cross-sectional view of the tonometric catheter illustrating a first means for attachment of an electronic field effect transistor sensor;

FIG. 2B is a partial cross-sectional view of the tonometric catheter illustrating a second means of attachment of the field effect transistor sensor;

FIG. 4A is a cross-sectional view of the tonometric catheter of FIG. 4 taken substantially along the line 4A—4A of FIG. 4;

FIG. 4B is a cross-sectional view of the tonometric catheter of FIG. 4 taken substantially along the line 4B—4B of FIG. 4;

FIG. 5A is a cross-sectional view of the tonometric catheter of FIG. 5, taken substantially along the line 5A—5A of FIG. 5;

FIG. 11 is another embodiment of a tonometric catheter with a urinary catheter;

FIG. 11A is a cross-sectional view of the tonometric catheter/urinary catheter of FIG. 11, taken substantially along the line 11A—11A of FIG. 11.

FIG. 12 is yet another embodiment of the tonometric catheter having an automatic sampling system.

DESCRIPTION OF THE PREFERRED EMBODIMENTS

Figure 3:
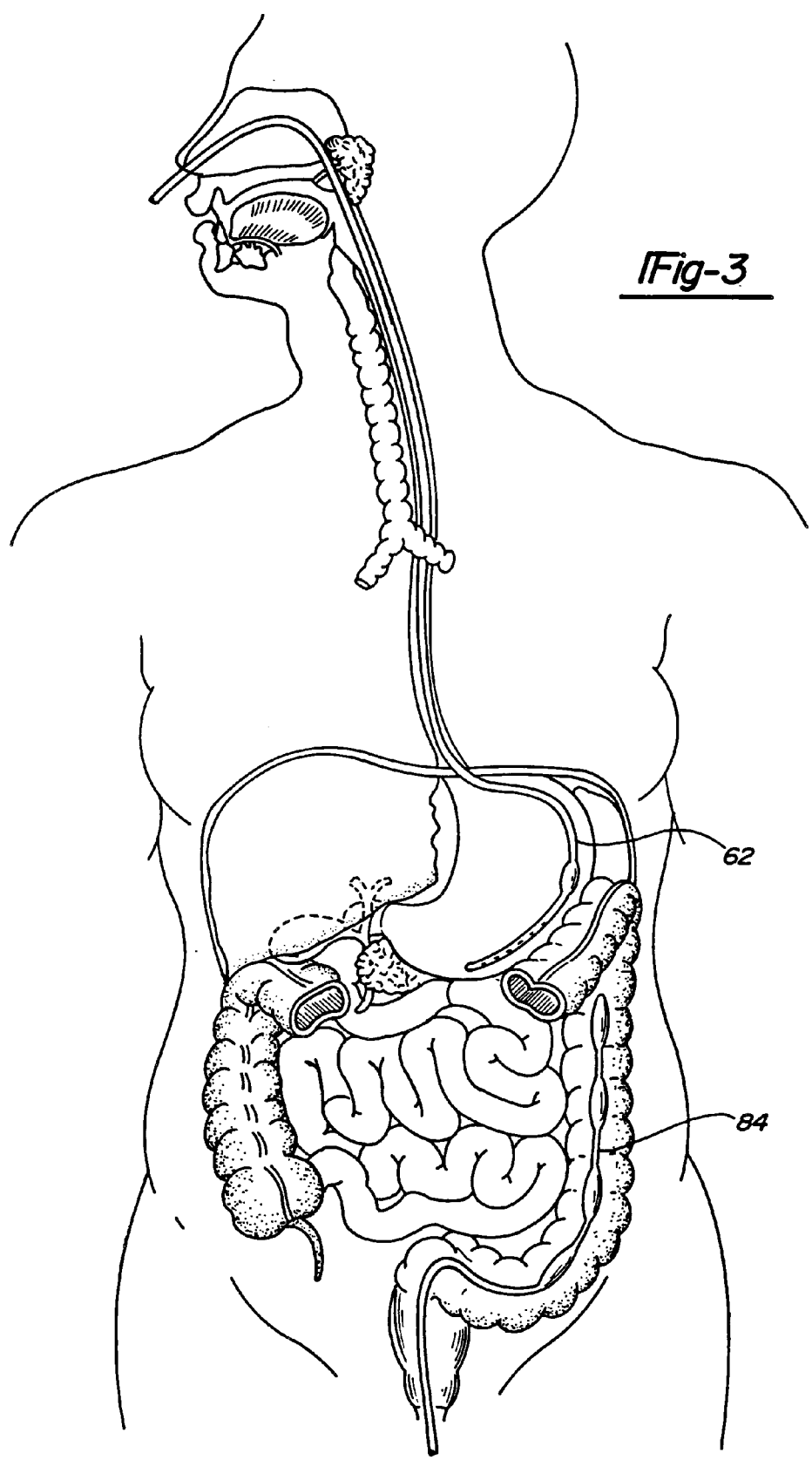
FIG. 3 illustrates the method of use of the tonometric catheter in measurement of the pH of the colon and also of the stomach, the specific embodiment illustrated for colonic measurement being that of FIG. 5 and the specific tonometric catheter for gastric measurement being that of FIG. 4.

FIG. 1 illustrates a first embodiment of tonometric catheter 20. The tonometric catheter comprises a length of suitable tubing 22, one end 32 of which is closed, and the opposite end of which has a connector such as a luer-lock 24. Luer-lock 24 is adapted to receive a complementary fitting 26, which in turn couples through a second length of tubing 28 to a three-way stopcock 30. Three-way stopcock 30 may be used to selectively connect tubing 28 to various sources of irrigation or aspiration.

Adjacent the closed end 32, tubing 22 is perforated as at 34. A balloon-like tonometric catheter membrane 36 is fitted over the closed end so that the perforations 34 are enclosed, as illustrated. The tonometric catheter membrane 36 has an internal sleeve diameter at 38 which forms a tight fit with tubing 22. The preferred form of tonometric catheter membrane is polydimethylsiloxane elastomer. The membrane may be sealed to the tubing 22 with appropriate adhesive so that the tonometric catheter membrane is sealed in a closed relationship to the outer wall of tubing 22, thereby forming a sampling chamber 40 adjacent closed end 32. The tonometric catheter membrane has a certain elasticity to allow the membrane to expand when filled with an aspirating liquid in order to contact the wall of the organ under examination, as will be explained below.

The membrane 36 is preferably constructed such that at least a portion of it is selectively permeable to the gas or fluid property of interest. In a preferred embodiment, it is selectively permeable to hydrogen, oxygen, or $H^+$, so that pH, $pCO_2$ and/or $pO_2$ can be measured. It is also preferably impermeable to other materials that would interfere with the desired measurements, such as other gases, proteins, and the like. In a highly preferred embodiment, an ion-selective membrane is employed.

Bonded to either the inner wall or the outer wall of tubing 22 are one or more sensors 42 for detecting a property indicative of pH and/or temperature. Two such sensors are illustrated in FIG. 1, bonded to the outside wall of tubing 22 with suitable adhesive. FIGS. 2A and 2B illustrate two alternate means of sensor attachment, FIG. 2A illustrating the sensor attached to the inner wall of tubing 22 and FIG. 2B illustrating the sensor attached to the outer wall of tubing 22.

In a preferred embodiment, at least a portion of the tubing, but not all of it, is made of a $CO_2$ impermeable material, such as polyester elastomers derived from the reaction of dimethylterephtalate 1,4-butanediol and α-hydro-Ω-hydroxypoly (oxytetramethylene). In a highly preferred embodiment, this is a material such as Hytril, sold by DuPont.

For purposes of sensing temperature, thermistor devices are presently preferred. For sensing properties indicative of pH chemically responsive field effect transistors or "Chemfets" may be employed. In this regard, Chemfet sensors 44 have been illustrated in FIGS. 2A and 2B. Chemfet sensor 44 comprises a field effect semiconductor device 46, which is encapsulated in a solution impervious material 48, such as a polymerized epoxy resin. The encapsulation material 48 in turn may be encapsulated in a housing 50 (FIG. 2A). Semiconductor device 46 is electrically coupled by bonding wires 52 to a terminal 54. Suitable electrical conductors such as conductor 56 are attached to terminal 54 for electrically communicating between the Chemfet device 44 and the electronic circuitry described below in connection with FIG. 9. Conductor 56 is preferably routed through tubing 22 and exits through a sealed aperture at or near the luer-lock end of tubing 22, as at 58. A more detailed description of a suitable electronic sensor may be found in U.S. Pat. No. 4,020,830 to Johnson, entitled "Selective Chemical Sensitive FET Transducers," incorporated herein by reference. In order to allow a solution to contact the chemically sensitive surface of semiconductor device 46, tubing 22 may be provided with an aperture 60 when implementing the embodiment of FIG. 2A. Such an aperture is not needed in the embodiment of FIG. 2B, since the semiconductor device 46 is exposed to sampling chamber 40 by virtue of the external mounting configuration.

The sampling chamber 40 can be filled with an aspiration or sampling medium that is used to absorb or otherwise provide a means for incorporating and delivering or measuring the the fluids or gases of interest. Such a medium is selected depending upon many factors, including the properties of the fluids or gases of interest, the type of sensor 42 employed, and the type of calibration that is necessary. Such mediums include bicarbonate solutions and saline solution. It might be noted that gases often behave as fluids and are therefore frequently considered to be fluids.

As noted above, when the sensor employed does not require frequent recalibration, the need for the sampling chamber 40 to be in communication with the proximate end of the tonometric catheter (that remains outside the patient) may be eliminated since no aspiration is needed. However, in many instances such communication may still be desirable as aspiration may be required to calibrate the sensor or sensors, to replace the aspirating or sampling medium with a fresh medium, and to incorporate the gas or gases of interest.

Figure 4:
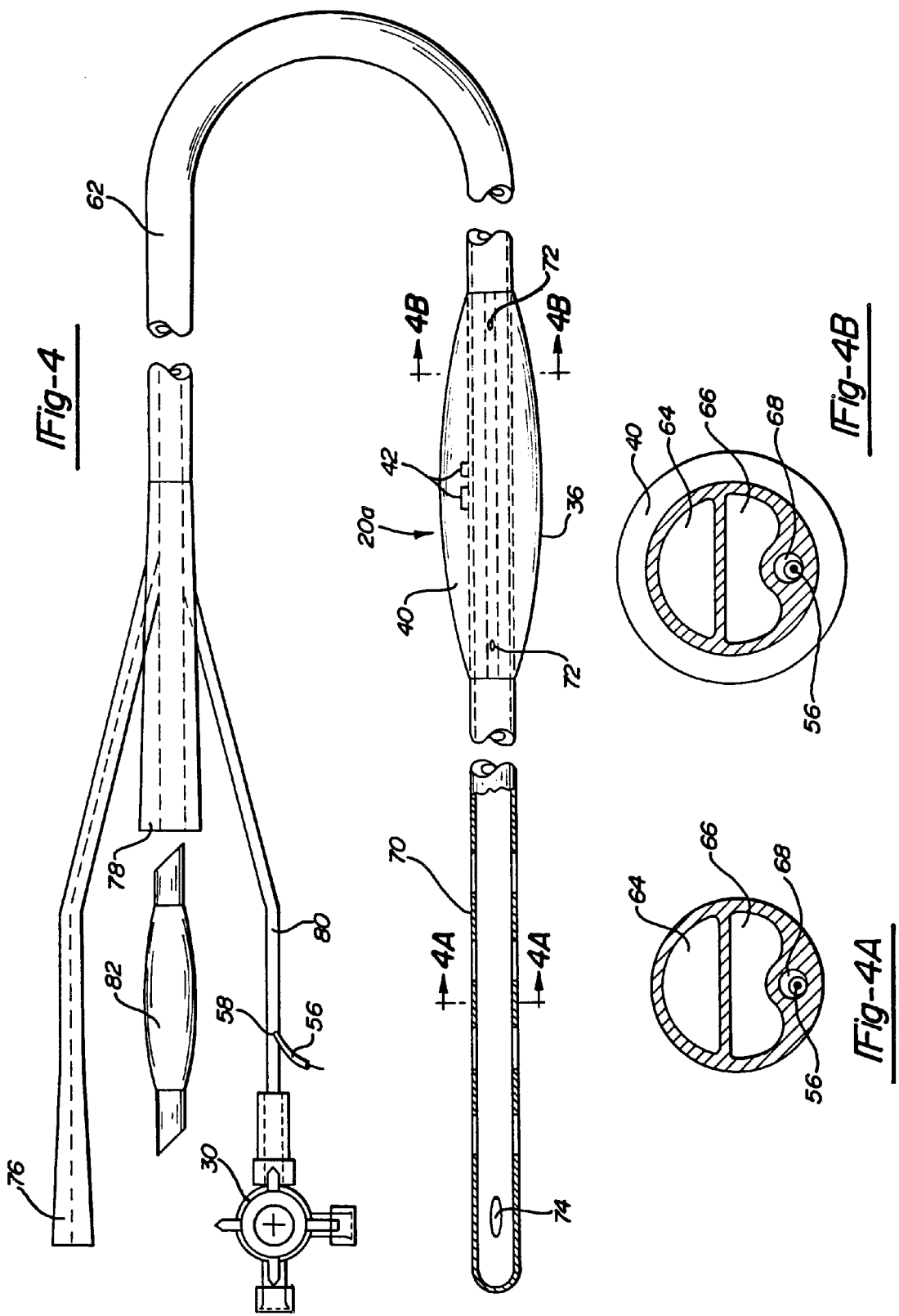
FIG. 4 is another embodiment of the tonometric catheter with nasogastric tube.

Another embodiment of the tonometric catheter is illustrated in FIGS. 4, 4A and 4B. As illustrated, the tonometric catheter is appropriately configured to also serve as a nasogastric sump, either with or without gastric suction. With reference to FIG. 4, the tonometric catheter 20a comprises a multipassage tubing 62 which defines three individual noncommunicating (between each other) passageways or lumens, an air lumen 64, an optional suction lumen 66 and a tonometric catheter lumen 68. A tonometric catheter membrane, similar to that previously described, is attached at an intermediate location on tubing 62, allowing a portion of the tubing to extend beyond the end of membrane 36 to define the nasogastric sump 70. Tubing 62 is provided with a plurality of perforations 72 which communicate between tonometric catheter lumen 68 and the sampling chamber 40 defined by membrane 36. If desired, one or more sensors 42 can be included in accordance with the above teachings, in which case a suitable conductor 56 may be routed through tonometric catheter lumen 68 to exit at sealed aperture 58.

The nasogastric sump portion 70 is suitably provided with a plurality of openings 74 through which the stomach may be aspirated.

At the opposite end of tubing 62 the tubing splits to form three separate connections. Air lumen 64 communicates with air lumen passageway 76, suction lumen connects with suction lumen passageway 78 and tonometric catheter lumen 68 communicates with tonometric catheter lumen passageway 80. The tonometric catheter lumen passageway is fitted with three-way stopcock 30, similar in function and purpose to the three-way stopcock 30 described in connection with FIG. 1. If desired, a quick connect fitting 82 may be used to couple the suction lumen passageway 78 with an aspiration source. As illustrated, the quick connect fitting preferably has angularly cut ends and a slightly enlarged midsection, making it easy to insert into the end of passageway 78 and also into the aspiration hose coupling (not shown). The enlarged midsection helps form a seal with the adjoining passageways. Preferably the quick connect fitting is fabricated of disposable plastic.

Figure 5:
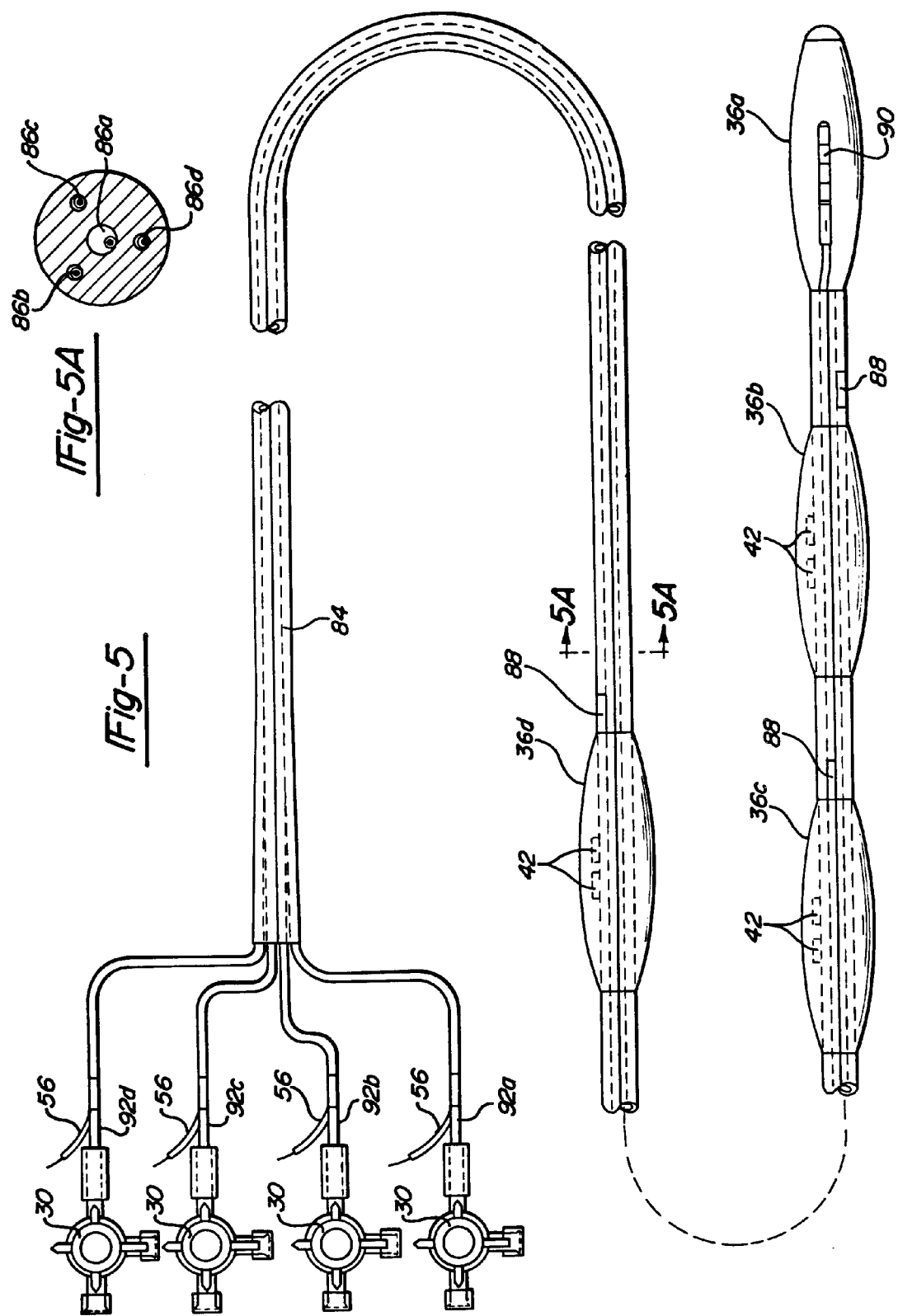
FIG. 5 is yet another embodiment of the tonometric catheter having multiple sensing/sampling portions.
Figure 6:
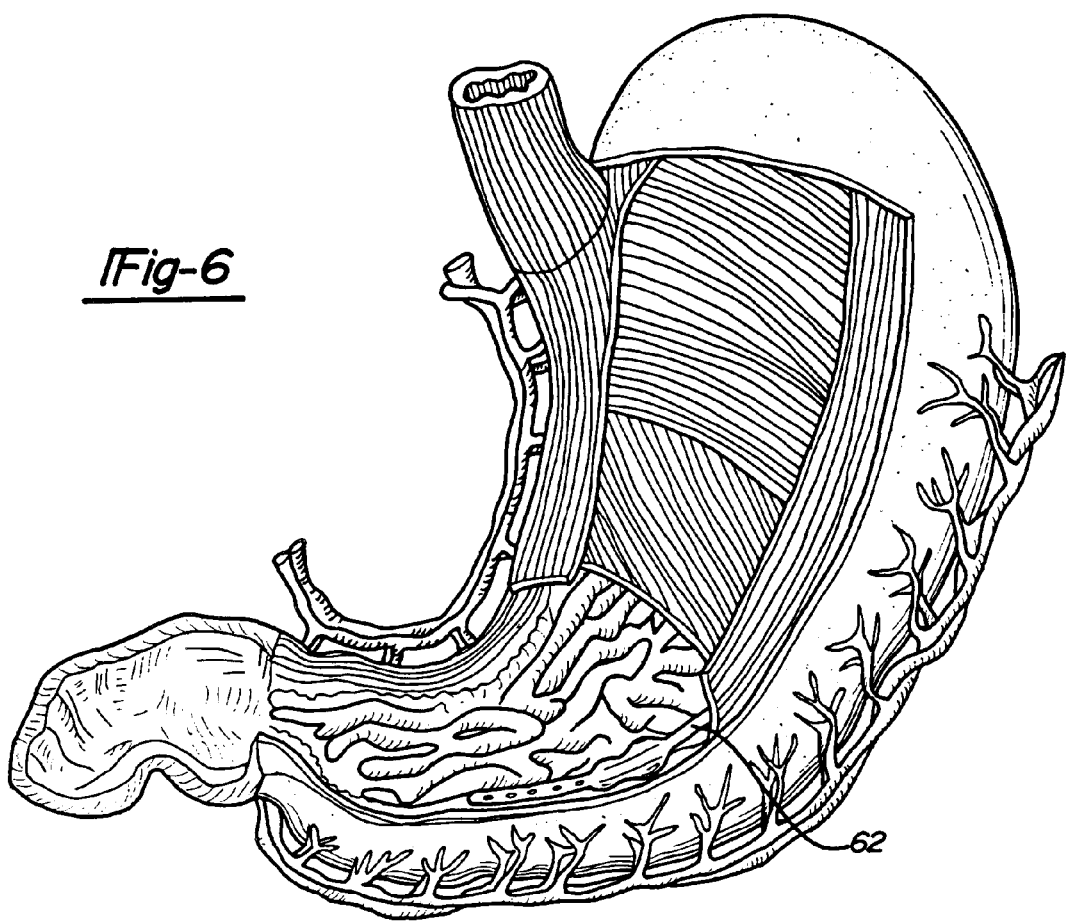
FIG. 6 is a detailed view illustrating the tonometric catheter of FIG. 4 in use within the stomach.

Yet another embodiment of the tonometric catheter is illustrated in FIGS. 5 and 5A. This embodiment is a multiple tonometric catheter embodiment employing a tubing 84 having a plurality of passageways or lumen as shown in the cross-sectional view of FIG. 5A. Specifically, tubing 84 includes an air lumen 86a which communicates with the endmost tonometric catheter 36a and three additional tonometric catheter lumens 86b, 86c and 86d, which communicate respectively with tonometric catheters 36b, 36c and 36d. As with the other embodiments, each tonometric catheter may be provided with one or more sensors such as sensors 42. A radiopaque tungsten plug 88 is positioned within each of the three tonometric catheter lumen 86b, 86c and 86d adjacent the distal end of each tonometric catheter, serving to block the remainder of the tonometric catheter lumen passageway and thereby ensuring that fluid pressure introduced into each tonometric catheter lumen will cause the associated tonometric catheter to balloon outwardly as required during use. Similarly, a radiopaque tungsten rod 90 is fitted as a plug in the end of air lumen 86a, serving to terminate the end of the air lumen passageway. Being radiopaque, the tungsten plugs and tungsten rod aid in properly positioning the tonometric catheters by being visible under fluoroscope or x-ray. In addition, if desired, tubing 84 can be provided with a radiopaque stripe along all or part of its length.

At the proximal end of tubing 84 the lumen 86a–86d diverge to define four separate tubes 92a–92d. Each tube is fitted with a three-way stopcock similar to those described above. Each sampling connector may optionally be coded numerically by color, etc. While four approximately equally spaced tonometric catheters have been illustrated in FIG. 5, it will be understood that the invention can be modified to include a greater or fewer number of tonometric catheters at different spacing as required for a particular application. It will also be understood that some or all of the tonometric catheters can include one or more sensors coupled to conductors 56, each preferably routed through the corresponding lumen passageway.

Figure 9:
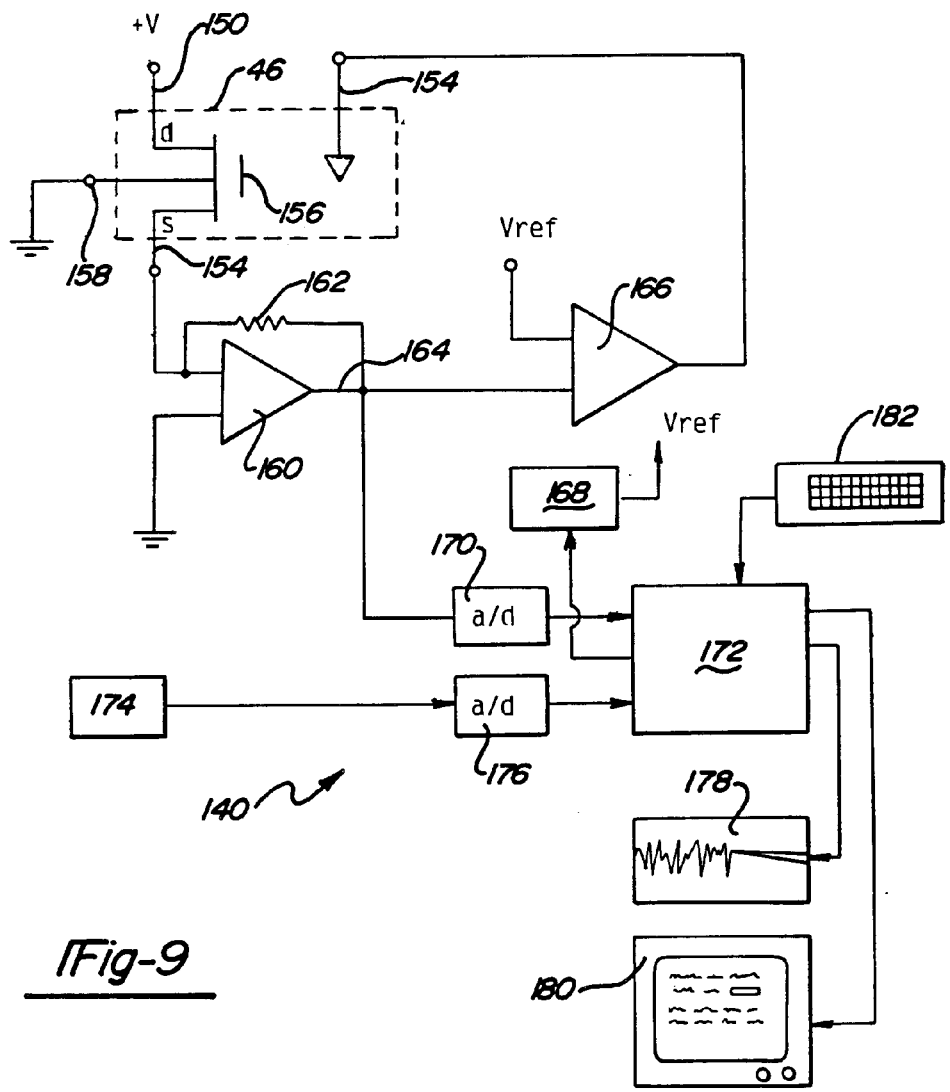
FIG. 9 is an electrical schematic diagram illustrating one embodiment of electronic circuit in accordance with the invention.

Referring now to FIG. 9, a suitable electronic monitoring circuit will now be described. In FIG. 9 CHEMFET semiconductor device 46 has been shown schematically by the equivalent circuit model enclosed in dotted lines. The device 46 thus comprises drain electrode 150, source electrode 152 and reference electrode 154. The chemically selective system, such as a membrane system is depicted diagrammatically at 156. The substrate is grounded as at 158.

Source electrode 154 is coupled to an input lead of operational amplifier 160 which includes feedback network diagrammatically depicted at 162. Operational amplifier 160 senses the drain source current flowing through device 46 and converts this signal into a voltage signal which is output on lead 164. The drain source current changes in accordance with changes in the chemical system under test. More specifically, as the $pCO_2$ level changes in the fluid exposed to device 46, the drain source current changes accordingly. Hence the output voltage signal on lead 164 is likewise an indication of the $pCO_2$ level of the organ under test. This voltage signal on lead 164 is coupled to an input of comparator 166 which also receives a reference voltage $V_{ref}$, which may be supplied using a voltage divider network (not shown) or which may alternatively be provided by a digitally controlled voltage source 168. The output of comparator 166 is fed to reference electrode 154 to provide a stable reference bias voltage. If a digitally controlled voltage source is used, this reference voltage can be adjusted and calibrated by a computer circuit yet to be discussed. The voltage signal on lead 164 is also fed to an analog to digital convertor 170, which is in turn coupled to a microprocessor-based microcomputer 172.

In order to automatically determine the pH of the wall of the hollow viscous organ under test, a separate gas analyzer sensor 174 is used to determine the bicarbonate concentration in the arterial blood of the patient. The output of sensor 174 is coupled through analog to digital convertor 176 to microcomputer 172. Microcomputer 172 is preprogrammed to calculate the pH of the organ wall using the values provided by analog to digital convertors 170 and 176. Conversion of $pCO_2$ measurements can be converted into pH measurements automatically by microcomputer 172 using various equations and references well-known in the art.

Although many different types of output devices may be employed, strip chart recorder 178 and CRT monitor 180 have been illustrated. Strip chart recorder 178 and monitor 180 are coupled as output devices to microcomputer 172. Strip chart recorder 178 offers the advantage of developing an easily readable, permanent record of the fluctuations in organ wall pH. Monitor 180 offers the advantage of providing digital readout of the pH value as well as displaying the upper and lower excursions of pH fluctuation. If desired, microcomputer 172 can be preprogrammed using keyboard 182 to compare the instantaneous pH value with doctor-selected upper and lower alarm limits. If the measured instantaneous pH fluctuates outside those limits, microcomputer 172 can sound an alarm to alert hospital staff.

While a single semiconductor device 46 has been illustrated in conjunction with the electronic circuit of FIG. 9, the circuit may be readily adapted for use with a plurality of semiconductor devices in order to measure the pH at different locations substantially simultaneously. In such an embodiment, the data coming from each sensor can be fed to a separate I/O port of microcomputer 172. In the alternative, a single I/O port can be used with the individual input signals being time multiplexed.

Figure 7:
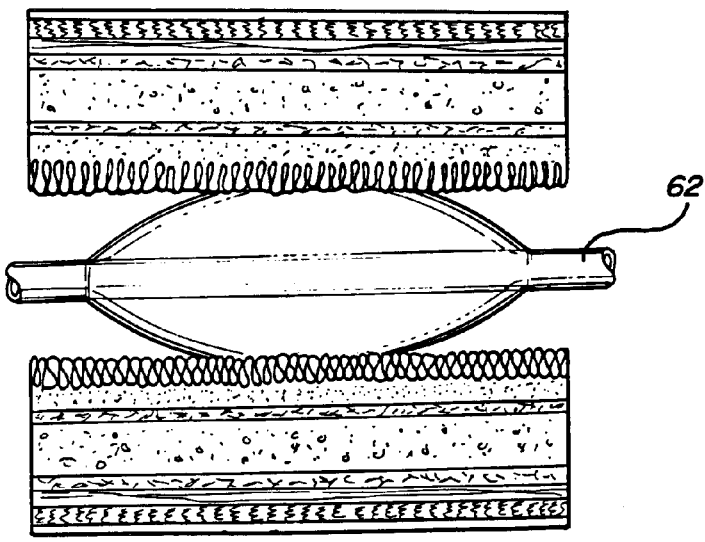
FIG. 7 is a detailed view illustrating the tonometric catheter of FIG. 5 in use within the colon.
Figure 8:
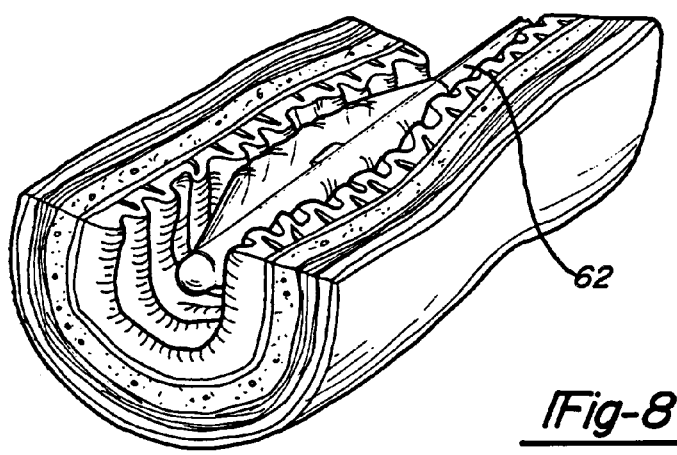
FIG. 8 is a similar view illustrating the tonometric catheter of FIG. 1 in use within the colon.
Figure 10:
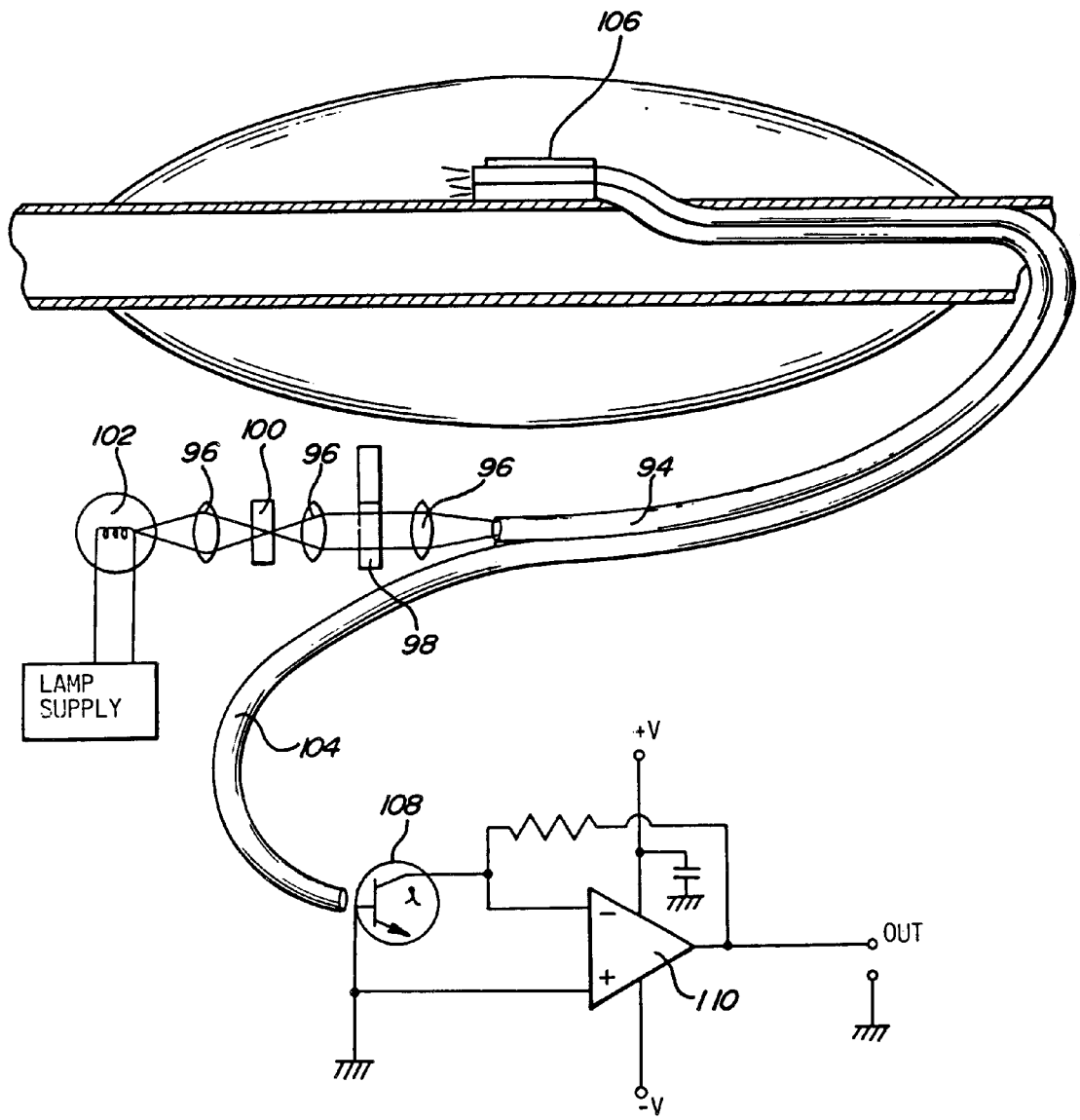
FIG. 10 is an electrical schematic diagram illustrating another embodiment of the optical measurement of pH in accordance with the invention.

As an alternative to electronic pH sensors, the invention may also be practiced using optical sensor technology. Referring to FIG. 10, the presently preferred optical sensor embodiment uses a first fiber optic cable 94 which is optically coupled through a series of lenses 96, selectable color filters 98 and heat absorber 100 to an illumination source 102, such as a 100 watt tungsten-halogen lamp. Fiber optic cable 94 is routed through the tonometric catheter lumen in a fashion similar to the conductor 56 of the above-described embodiments, with the end thereof protruding through the tubing and into the sampling chamber 40. A second fiber optic cable 104 is routed parallel to the first fiber optic cable 94, with one end protruding through the tubing and held in place adjacent the end of first cable 94 with a collar 106. Collar 106 may be adhesively bonded to the outside wall of the tubing. The opposite end of second fiber optic cable 104 is positioned for optically coupling with a phototransistor 108 which is electrically connected to an operational amplifier circuit 110. The operational amplifier circuit can be coupled to an analog to digital converter, such as A/D converter 170 of FIG. 7.

In use, fiber optic cable 94 illuminates a region within the sampling chamber 40 which is filled with a sampling fluid containing a calorimetric pH indicator. The illumination from fiber optic cable 94 reflects from the molecules suspended in the pH indicator solution, with some of the reflected illumination passing back through second fiber optic cable 104 to the phototransistor. By selecting the appropriate filter 98, a monochromatic illumination or illumination of otherwise known spectral content is employed to illuminate the calorimetric pH indicator solution. When the color of the filtered illumination matches that of the indicator, the illumination is absorbed and a low illumination signal is received at the phototransistor. When a pH change causes a color change in the indicator away from the color of the filtered illumination, more illumination is reflected back to the phototransistor, with an attendant increase in detected signal output. In this fashion, the proper selection of indicator dye and illumination filtration can be used to detect pH ranges. For a further description of fiber optic pH sensor technology, refer to G. G. Vurek "A Fiber Optic $pCO_2$ Sensor," *Annals of Biomedical Engineering*, Vol. 11, pp. 499–510, 1983, which is available from Pergamon Press, Ltd., and is expressly incorporated herein by reference.

While the preferred embodiments have been disclosed in connection with monitoring of the gastrointestinal tract and the urinary and ureteric tracts it will be appreciated that its principles are applicable to other hollow internal organs to monitor pH and hence perfusion of those organs. Also while several presently preferred detailed constructions for tonometric catheters have been disclosed, it will be appreciated that other constructions may be developed which are equally suitable. The disclosed constructions are presently preferred for the reason that they are readily fabricated using existing available materials. Other embodiments may include other, but equivalent materials for the tonometric catheter membrane and/or connective tubing. They may also differ in the specific fabrication details. As an example, the sampling chamber may be eccentric rather than symmetric about the connective tubing.

In still another embodiment, conventional gas analyzers may be employed externally. A device such as that shown in FIG. 1 may be used in combination with a pump or aspiration means (not shown) for continuous or regular intermittent aspiration of a sample of the aspirating liquid or medium that is used to fill the sampling chamber 40. The sample removed by pump or aspiration means via attachment to the luer-lock 24 can be optionally designed so that the sample aspirated at each sampling interval can be brought in contact with an exterior, separate gas analyzing means or sensor (not shown) to determine the pH, $pO_2$, $pCO_2$ and/or the like, of the sample. Such automatic sampling can be conducted employing a system as shown in FIG. 12. In the assembly a sampling system employs a personal computer to conduct evaluations and analysis of the samples withdrawn from the tonometric catheter 299.

Pump 203 is loaded with the sampling or aspirating medium such as saline. Next, valve 201 is activated to withdraw a desired amount of the sampling fluid. The valve 201 is deactivated and pump 203 is used to enforce the sampling chamber of the tonometric catheter 299 using a calibrated amount or optionally a pressure transducer 215. The sampling fluid or medium is allowed to come to equilibrium with the wall of the organ or area of interest. Next the "dead space," i.e., the area of the lumen filled with the sampling fluid that is not in equilibrium, is removed by activating valve 205, activating pump 207, activating valve 209 and infusing pump 207; the waste 219 is discarded. A sample for analysis is then withdrawn by deactivating valve 209, activating pump 207 to then deliver the sampling to a gas analyzer (not shown) that provides data from the sample to the PC 217, and the evaluation is conducted as described herein.

The sample gas analyzer or a separate gas analyzer may be employed to determine the bicarbonate concentration in the arterial blood of the patient, as described above.

Another embodiment of the tonometric catheter is illustrated in FIGS. 11 and 11A. As illustrated, the tonometric catheter is appropriately configured to also serve as a urinary or ureteric catheter, either with or without suction, which optionally employs sensors. With reference to FIGS. 11 and 11A, the tonometric catheter 220 comprises a multipassage tubing 262 which defines three individual noncommunicating (between each other) passageways or lumens, an optional air or irrigation lumen 264, a drainage or auction lumen 266 and a tonometric catheter lumen 268. A tonometric catheter membrane, similar to that previously described, is attached at a distal location on tubing 262, allowing an intermediate portion of the tubing not extending beyond the end of membrane 236 to define the uretary or uretary catheter 270. Tubing 262 is provided with a plurality of perforations 272 which communicate between tonometric catheter lumen 268 and the sampling chamber 240 defined by membrane 236. If desired, one or more sensors 242 can be included in accordance with the above teachings, in which case a suitable conductor 256 may be routed through tonometric catheter lumen 268 to exit at sealed aperture 258.

The urinary catheter or ureteric catheter portion 270 is suitably provided with a plurality of openings 274 through which the bladder or ureters may be aspirated or irrigated.

At the opposite end of tubing 262 the tubing splits to form three separate connections. Air or irrigation lumen 264 optionally communicates with air lumen passageway 276, urinary lumen connects with suction or drainage lumen passageway 278 and tonometric catheter lumen 268 communicates with tonometric catheter lumen passageway 280. The tonometric catheter lumen passageway is fitted with three-way stopcock 230, similar in function and purpose to the three-way stopcock 30 described in connection with FIG. 1. If desired, a quick connect fitting 82 as seen in FIG. 4 may be used to couple the suction urinary passageway 278 with an aspiration source. As illustrated, the quick connect fitting preferably has angularly cut ends and a slightly enlarged midsection, making it easy to insert into the end of passageway 278 and also into the aspiration hose coupling (not shown). The enlarged midsection helps form a seal with the adjoining passageways. Preferably the quick connect fitting is fabricated of disposable plastic.

Yet another embodiment of the urinary catheter/tonometric catheter combination illustrated in FIGS. 11 and 11A may employ a multiple tonometric catheter embodiment employing a tubing having a plurality of passageways or lumen as shown in the cross-sectional view of FIG. 5A.

In another embodiment of the present invention, a tonometric catheter may be adopted to deliver a pharmaceutically-active agent, either for systemic, local or topical activity, or a combination thereof. For example, an additional lumen may be added such as that and for irrigation or aspiration, to deliver the active. For example, the irrigation/aspiration lumen 264 shown in FIGS. 11 and 11A, may be used to deliver an active agent. In another embodiment, a portion of the device may be modified so as to provide sustained release of the active agent of interest.

Thus, for example, the problems of nosacomial infection associated with catheter insertion can be overcome by incorporating an antimicrobial into at least a portion of the polymeric material used to manufacture the tonometric catheter, or by coating at least a portion of the device with a sustained release composition, or by delivering the antimicrobial via the tonometric catheter. Such modifications are well known to those skilled in the art. See U.S. Pat. No. 4,677,143, incorporated herein by reference.

Classes of useful agents include antimicrobial agents, nonsteroidal anti-inflammatory agents, topical anesthetics, topical vasodialators, metabolic suppressants, and other agents that could be delivered for absorption at the sites of the tonometric catheter.

Accordingly, while several preferred embodiments of the invention have been disclosed, it will be appreciated that principles of the invention, as set forth in the following claims, are applicable to other embodiments.

What is claimed is:

1. A method for measuring partial pressure of one or more gases in the gastrointestinal lumen of a patient comprising the steps of:
    A. defining an intraluminal region as a region-of-interest within the gut of a patient by inserting a catheter into said patient, said catheter having a distal end and a proximal end, whereby said distal tip is located in a desired intraluminal region in the gut of said patient and said proximal end is external to said patient, and wherein said catheter further includes an open-faced chamber defined near the distal end of said catheter, and a gas permeable membrane spanning said open-faced chamber to define a closed gas-filled gas sensing region therein, said closed gas sensing region having substantially no fluidic communication with said proximal end, and includes a detector, said detector including a $CO_2$ sensor affixed to said catheter near said distal end and including selectively operative sensor means for generating at said proximal end a signal representative of the concentration of $CO_2$ in said intraluminal region adjacent to said distal end,
    B. sensing in said gut the concentration of said gases in said region-of-interest, and
    C. generating a signal representative of said concentration, said signal being representative of the partial pressure of said gases in said region-of-interest, wherein said sensing step and said generating step include the step of operating said sensor means.

2. The method of claim 1 wherein said gases include one or more gases selected from the group consisting of carbon dioxide ($CO_2$) and oxygen ($O_2$).

3. The method of claim 2 wherein the number of gases measured is greater than 1, and wherein said method includes the step of sensing in said gut the partial pressure of said gases with separate sensors.

4. The method of claim 1 wherein said detector further includes an $O_2$ sensor affixed to said catheter near said distal end and including selectively operative sensor means for generating at said proximal end a signal representative of the concentration of $O_2$ in said intraluminal region adjacent to said distal end, and
    wherein said sensing step and said generating step include the step of operating said sensor means.

5. An intraluminal gastrointestinal gas measuring system, comprising:
    A. an elongated catheter having a distal end and a proximal end,
    B. one or more gas sensors affixed to said catheter near said distal end, wherein at least one of said gas sensors includes a sampling chamber defined near the distal end of said catheter, and a gas permeable membrane spanning said chamber to define a closed fluid filled gas sensing region therein, said closed gas sensing region having substantially no fluidic communication with said proximal end, and wherein at least one of said gas sensors is adjacent to said closed gas sensing region and in optical communication with said proximal end, and
    C. sensor means for generating at said proximal end a signal representative of the partial pressure of said gases external to said catheter and adjacent to said gas sensors.

6. A measuring system according to claim 5 wherein at least one of said sensors is a $CO_2$ sensor.

7. A measuring system according to claim 6 wherein at least one of said sensors is an $O_2$ sensor.

8. A measuring system according to claim 6 wherein said sensor means is selectively operative and includes:
    A. a first optically transmissive optical fiber extending from a first point at the boundary of said gas sensing region to said proximal end,
    B. a second optically transmissive optical fiber extending from a second point at the boundary of said gas sensing region to said proximal end, said first optical fiber at said first point being optically coupled to said second optical fiber at said second point,
    C. means for directing optical radiation through said first fiber from a point near said proximal end toward said gas sensing region, and
    D. means for detecting at a point near said proximal end optical radiation coupled from said first fiber across said gas sensing region to said second fiber and through said second fiber.

9. A system according to claim 8 wherein said sensor means further comprises means coupled to said second fiber near said proximal end for determining gas concentration in said gas sensing region from said detected optical radiation.

10. A measuring system according to claim 9 wherein said catheter further comprises
    A. first calibration lumen extending from said proximal end to and in selective communication with said chamber of said sensor,
    B. second calibration lumen extending from said proximal end to and, in selective communication with said chamber of said sensor,
    C. means for selectively passing a calibration gas through said first calibration lumen and said chamber to said second calibration lumen, and
    D. means for operating said sensor means while said calibration means is passing said calibration gas through said sensing region.

11. A measuring system according to claim 9 wherein said catheter further includes at least one open ended lumen extending between said distal end and said proximal end.

12. A measuring system according to claim 5 wherein said catheter further includes at least one open ended lumen extending between said distal end and said proximal end.

13. An intraluminal gastrointestinal gas measuring system, comprising:
    A. an elongated catheter having a distal end and a proximal end,
    B. one or more gas sensors affixed to said catheter near said distal end, wherein at least one of said gas sensors includes an open-faced chamber defined near the distal end of said catheter, and a gas permeable membrane spanning said open-faced chamber to define a closed gas-filled gas sensing region therein, said closed gas sensing region having substantially no fluidic communication with said proximal end, and wherein at least one of said gas sensors is adjacent to said closed gas sensing region and in optical communication with said proximal end, and C. sensor means for generating at said proximal end a signal representative of the partial pressure of said gases external to said catheter and adjacent to said gas sensors.

14. A measuring system according to claim 13 wherein at least one of said sensors is a $CO_2$ sensor.

15. A measuring system according to claim 14 wherein at least one of said sensors is an $O_2$ sensor.

16. A measuring system according to claim 14 wherein said sensor means is selectively operative and includes:

A. a first optically transmissive optical fiber extending from a first point at the boundary of said gas sensing region to said proximal end, B. a second optically transmissive optical fiber extending from a second point at the boundary of said gas sensing region to said proximal end, said first optical fiber at said first point being optically coupled to said second optical fiber at said second point, C. means for directing optical radiation through said first fiber from a point near said proximal end toward said gas sensing region, and D. means for detecting at a point near said proximal end optical radiation coupled from said first fiber across said gas sensing region to said second fiber and through said second fiber.

17. A system according to claim 16 wherein said sensor means further comprises means coupled to said second fiber near said proximal end for determining gas concentration in said gas sensing region from said detected optical radiation.

18. A measuring system according to claim 17 wherein said catheter further comprises A. first calibration lumen extending from said proximal end to and in selective communication with said chamber of said sensor, B. second calibration lumen extending from said proximal end to and, in selective communication with said chamber of said sensor, C. means for selectively passing a calibration gas through said first calibration lumen and said chamber to said second calibration lumen, and D. means for operating said sensor means while said calibration means is passing said calibration gas through said sensing region.

19. A measuring system according to claim 17 wherein said catheter further includes at least one open ended lumen extending between said distal end and said proximal end.

20. A measuring system according to claim 13 wherein said catheter further includes at least one open ended lumen extending between said distal end and said proximal end.

* * * * *